United States Patent [19]

Wartman

[11] Patent Number: 4,483,333

[45] Date of Patent: Nov. 20, 1984

[54] ORTHOPEDIC CAST

[75] Inventor: Lloyd H. Wartman, Eden Praire, Minn.

[73] Assignee: WRF/Aquaplast Corporation, Ramsey, N.J.

[21] Appl. No.: 383,758

[22] Filed: Jun. 1, 1982

[51] Int. Cl.³ .............................. A61F 5/04
[52] U.S. Cl. .................................... 128/90
[58] Field of Search .............................. 128/90

[56] References Cited

U.S. PATENT DOCUMENTS

| D. 239,143 | 3/1976 | Arluck et al. | D24/4 |
|---|---|---|---|
| 2,301,426 | 11/1942 | Lovell | 128/90 |
| 2,616,418 | 11/1952 | Eberl | 128/90 |
| 2,697,434 | 12/1954 | Rodman | 128/90 |
| 2,853,067 | 9/1958 | Puharich | 128/90 |
| 3,027,336 | 3/1962 | Götz et al. | 260/2.5 B |
| 3,111,469 | 11/1963 | Marans | 204/154 |
| 3,259,607 | 7/1966 | Cherdron et al. | 260/78.3 |
| 3,314,419 | 4/1967 | Quick | 128/90 |
| 3,373,741 | 3/1968 | Hill et al. | 128/90 |
| 3,420,231 | 1/1969 | Edenbaum | 128/90 |
| 3,442,265 | 5/1969 | Malven | 128/90 |
| 3,490,444 | 1/1970 | Larson | 128/90 |
| 3,592,190 | 7/1971 | Silverman | 128/90 |
| 3,632,687 | 1/1972 | Walter et al. | 525/186 |
| 3,656,476 | 4/1972 | Swinney | 128/90 |
| 3,662,057 | 5/1972 | Webster et al. | 264/321 |
| 3,692,023 | 9/1972 | Phillips et al. | 128/90 |
| 3,763,858 | 9/1973 | Buese | 128/156 |
| 3,809,600 | 5/1974 | Larson | 161/109 |
| 3,819,796 | 1/1974 | Webster et al. | 264/321 |
| 3,853,124 | 12/1974 | Larson | 128/90 |
| 3,906,943 | 9/1975 | Arluck | 128/90 |
| 3,908,644 | 9/1975 | Neinart et al. | 128/90 |
| 4,006,741 | 2/1977 | Arluck | 128/90 |
| 4,019,505 | 4/1977 | Wartman | 128/90 |
| 4,136,686 | 1/1979 | Arluck | 128/90 |
| 4,240,415 | 12/1980 | Wartman | 128/90 |
| 4,274,983 | 6/1981 | Kent | 128/90 |
| 4,286,586 | 9/1981 | Potts | 128/90 |

OTHER PUBLICATIONS

Union Carbide, New Polycaprolactone Thermoplastic Polymers PCL-300 & PCL-700 (F-42501).
Union Carbide, Polycaprolactone Polymer PCL-700 Biodegradation and Molding Information, F-44453.
Chemical Abstracts, vol. 72, p. 44.

Primary Examiner—C. Fred Rosenbaum
Assistant Examiner—Harrie R. Samaras
Attorney, Agent, or Firm—Blodgett & Blodgett

[57] ABSTRACT

An orthopedic cast made of a mixture of polyethylene and a thermoplastic polyester having a melting point between 50° C. and 100° C., particularly poly (epsilon-caprolactone), having a weight average molecular weight of over 5,000 with a half-time crystallization at 36° C. of between 0.5 minute and 10.0 minutes.

10 Claims, 4 Drawing Figures

ORTHOPEDIC CAST

BACKGROUND OF THE INVENTION

Plastic materials have been used successfully in the past to make formable splints and casts. Some of the plastics that have been used are polyisoprene (U.S. Pat. No. 3,490,444) and polychloroprene (U.S. Pat. No. 3,592,190). Copolymers of trioxane (U.S. Pat. No. 3,604,413) and several other thermoplastics have also been recommended. Recently, poly (epsilon-caprolactone) a crystalline polyester melting at 60° C., and its blends with poly-(vinyl alkyl ether) have been discovered to be excellent splint and cast materials (U.S. Pat. No. 3,692,023). Such a cast has been described in the Wartman U.S. Pat. Nos. 4,019,505 and 4,240,415. All these polymers have low softening temperatures. In addition, they harden slowly when cooled from the melt to below their softening temperature. They can be heated to a temperature higher than their softening point, allowed to cool in room air temperature, and then molded to the patient without causing discomfort.

Examination of prior art materials based on these polymers in their molten form indicates that they possess another property desirable for easy forming to a smooth surface with good conformity and a lack of wrinkles, indentations or other defects imparted by the hand molding. The molten products do not flow excessively when unsupported by a back-up film, an internal gauze or some such structure. Distortion of the physical dimensions of a molten polymer can take place through viscous flow, elastic flow, or a combination of the two. Some of the prior art products, such as those based on polyisoprene or poly-chloroprene, distort in part by elastic flow. If a strip of molten polymer is manually extended and then released, it has some tendency to return to its original dimensions. However, viscous flow also takes place and permanent distortion beyond the original dimensions occurs. Consequently, when forming these materials, a permanent decrease in thickness can take place. If the therapist inadvertantly stretches the material too much in forming it, the material becomes permanently elongated and unusable for the intended application. Also, reforming a splint, brace, or cast because of a loss of edema in the fitted body member is not possible because, while it is possible to enlarge the structure, reducing its dimensions is not feasible.

In order to provide as stable a structure as possible, so that excessive stretching does not occur in the molten state, the prior art materials generally contain submicron sized fillers such as fumed silica, asbestos, clay, or mica. These fillers exert a thixotropic effect and the viscosity, especially at low shear rates, is greatly increased.

This technique is also useful with poly (epsilon-caprolactone), but considerable quantities of filler are required. About 10% of fumed silica is needed to achieve the required viscosity, while even larger quantities of clay or mica must be employed. Compounding these fillers into the plastic requires sophisticated, costly equipment. The density of the resulting plastic is higher and this is undesirable, because the splint or cast is heavier. Also, the presence of the filler causes the melt to be opaque, so that there is no visual indication that the material has reached the proper temperature for application.

The fillers which are most effective in achieving the thixotropic melt behavior are those with the smallest average particle size. These specialized products are quite expensive and, generally, they do not serve to reduce the cost of the end product. It would be advantageous to achieve the proper rheological properties in the melt using a cheap, larger particle size filler such as calcium carbonate. Heretofore, this has not been feasible because the amounts necessary to attain the proper level of thixotropy are too great and result in a deterioration of the physical properties of the product. These and other difficulties experienced in the prior art materials have been obviated in a novel manner by the present invention.

With these and other objects in view, as will be apparent to those skilled in the art, the invention resides in the combination of parts set forth in the specification and covered by the claims appended hereto.

It is, therefore, an outstanding object of this invention to provide an orthopedic cast, splint, or brace which is clean and simple to apply.

A further object of this invention is to provide an orthopedic cast, which is elastic in the molten state and can be reformed to its pre-application shape by remelting and allowing to relax to its original geometry.

Another object of this invention is to provide a cast which has molding characteristics which are relatively insensitive to the temperature of heating and application.

Another object of this invention is to provide a cast which conforms readily to the irregular shapes of the body member to be fitted.

Another object of this invention is the provision of an orthopedic cast which can be applied in a short time.

A further object of the present invention is the provision of an orthopedic cast which is light, strong, and sanitary in use, which allows circulation of air under the cast, and which permits washing of the limb.

It is another object of the instant invention to provide an orthopedic cast which does not require cumbersome equipment to apply.

A still further object of the invention is the provision of an orthopedic cast which reliably adheres to itself during application.

It is a further object of the invention to provide an orthopedic cast which can be applied to the patient while the cast is still in a plastic state.

It is a still further object of the present invention to provide an orthopedic cast which can be pre-formed and which will maintain the pre-formed shape even when rendered plastic.

With these and other objects in view, as will be apparent to those skilled in the art, the invention resides in the combination of parts set forth in the specification and covered by the claims appended hereto.

SUMMARY OF THE INVENTION

This invention involves an orthopedic cast system in which a cast is formed by wrapping a sheet of thermoplastic which has been brought to its melting point around the patient's limb and allowing the sheet to cool to hardness. The sheet is preferably heated in water and bonds to itself while molten. The preferred thermoplastic is a mixture of polyethylene and poly (epsilon-caprolactone) having a weight-average molecular weight of over 5,000, having a melting point in the range from 50° C. to 100° C., and having a half-time crystallization at 36° C. of 0.5 to 10.0 minutes.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
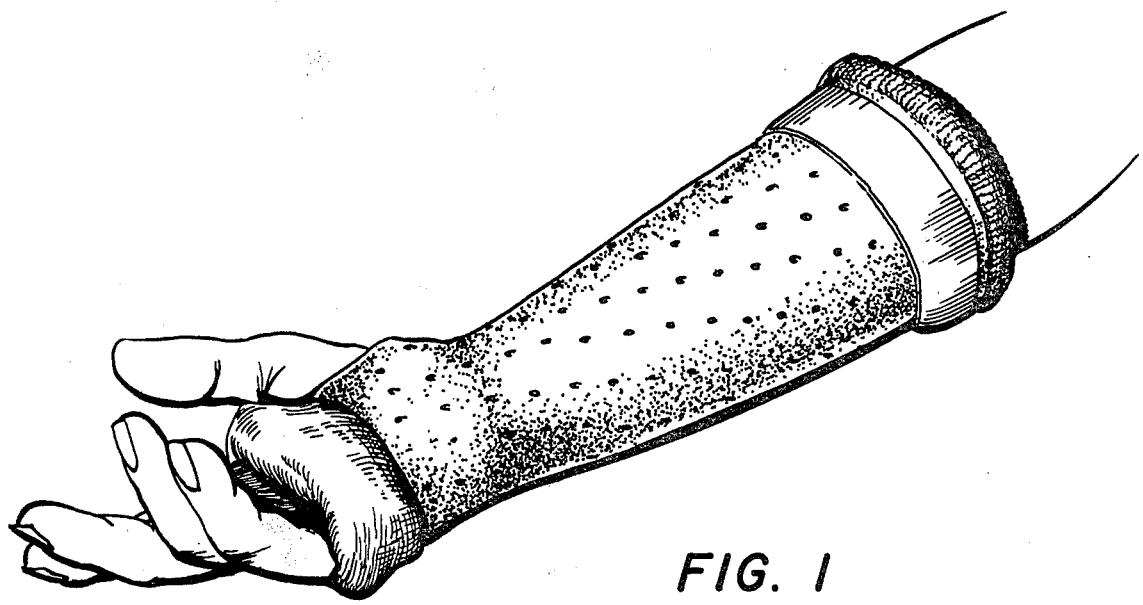
FIG. 1 is a perspective view of a wrist cast embodying the principles of the present invention in use on a human limb.

Referring to the drawings, FIG. 1 shows an orthopedic cast 10 in use on the arm of a human being.

Figure 2:
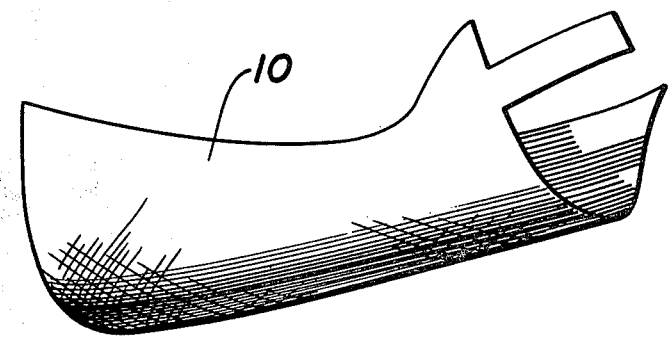
FIG. 2 is a perspective view of a pre-formed cast ready for heating and application.

FIG. 2 shows the cast 10 in a pre-formed condition, ready for application to a human limb.

Figure 3:
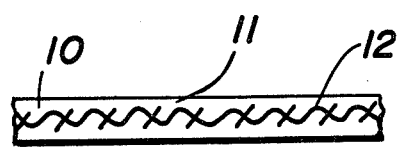
FIG. 3 is a cross-sectional view of a continuous composite sheet.

In FIG. 3, a cross-section of the cast is shown with a thermoplastic 11 applied to a substrate 12 to provide a closed cast.

Figure 4:
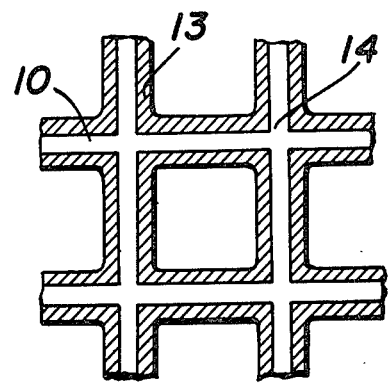
FIG. 4 is a cross-sectional view of a foraminous, composite sheet.

FIG. 4 shows a sectional view of the cast 10 with a thermoplastic applied in the form of a coating 13 to an open network substrate 14 to provide a foraminous cast.

The orthopedic cast is formed by wrapping a sheet of thermoplastic which has been brought to its melting point around the patient's limb and allowing the sheet to cool to hardness. The sheet is preferably heated in water and bonds to itself while molten. The preferred thermoplastic is a mixture of polyethylene and poly (epsilon-caprolactone) having a weight-averaged molecular weight of over 5,000, having a melting point in the range from 50° C. to 100° C., and having a half-time crystallization at human body temperature (36° C.) in the range from 0.5 to 10.0 minutes. The cast, formed of a mixture of polyethylene and a linear polyester poly (epsilon-caprolactone) in the form of sheets can be irradiated with electrons. At a 15 megarad dose, a continuous internal network is formed, as indicated by the elastic behavior of the molten polymer.

The following are examples of the operation of the invention:

A mixture containing 25% of a 20 melt index, 0.965 density polyethylene, 73% polycaprolactone, 2% triallyl cyanurate, and a trace concentration of Irganox 1010 anti-oxidant was compounded in an extruder. The temperature employed was above the melting temperature of the polyethylene component. The mixture was stranded and pelletized.

The mixture was then injection molded into plaques measuring 18" by 24" by ⅛". The 25% master batch was cut back with polycaprolactone, so that the final concentration of polyethylene in the various plaques was 25%, 20%, and 15%. The products were tested by placing strips in water at a temperature of about 70° C. All samples showed handling characteristics suitable for forming splints. Surprisingly, the hardening time was considerably reduced compared to that of cross-linked polycaprolactone. This is desirable, since hardening remains slow enough so that there is plenty of time to form the splint.

A mixture consisting of 10 melt index, high density polyethylene pellets and polycaprolactone pellets was formed into sheets without pre-compounding. The mixture of pellets was fed into the extruder of an injection molding machine, the only compounding action being that of the rotating screw. Homogenous, uniform plaques were obtained despite the absence of intensive compounding.

It can be seen, then, that the increased melt viscosity required for making a material which can be easily fabricated into a cast or splint is readily achieved by incorporating polyethylene in polycaprolactone. The mixture, which may contain other ingredients, such as anti-oxidants and cross-linking enhancers, is made by conventional melt processing techniques, utilizing a two-roll mill, a banbury or a compounding extruder. The temperature of processing must exceed the melting temperature of the polyethylene component.

In the melt compounding of mixtures of polymers, it is well-known that mixing is facilitated if the two polymers are reasonably close to the same melt viscosity at the temperature at which the compounding is done. The same holds true for mixtures of a single polymer where the components vary in melt viscosity. Thus, a 10 melt index polyethylene readily mixes with a 20 melt index polyethylene, whereas high intensity mixing and longer compounding times are required to mix a 0.1 melt index polyethylene with a 20 melt index polyethylene. Trial mixings have shown that very intensive mixing and long compounding times are needed to mix a 0.1 melt index polyethylene with polycaprolactone, whereas a 20 melt index polyethylene mixes quite readily.

The mixture of polyetheylene and polycaprolactone are not homogeneous. Each polymer remains as a separate phase. If the mixture is heated to a temperature higher than the 60° C. melting temperature of polycaprolactone but lower than the melting temperature of the polyethylene component, a two phase system consisting of molten polycaprolactone and solid polyethylene results. Apparently, at these temperatures the polyethylene acts as a finely-divided filler in the polycaprolactone and imparts a thixotropic effect, thus increasing the viscosity, especially at low shear rates.

Polyethylene is available in a range of densities, depending on the degree of branching of the polymer chains. High degrees of branching result in low crystallinity and low density. The tensile modules increases with increasing density from a low of 15,000 psi at 0.915 density to 170,000 psi at 0.965 density. Since one desires a high stiffness in a cast or splint material, the high density polyethylene mixtures make the most desirable product. For the purpose of this invention, high density polyethylene shall be defined as polyethylene having a density of 0.940 or greater. The preferred density for polyethylene used in this invention is approximately 0.965. While unmodified polycaprolactone has a modulus of 50,000 psi, the inventive mixture using 25% high density polyethylene has a modulus of 70,000 psi.

In some cases it may be desirable to impart some elasticity to the mixture by using the electron radiation technique described in the Wartman U.S. Pat. No. 4,240,413. In this way both a thixotropic and an elasticity effect can be achieved. Fortunately, polyethylene (in contrast to most polymers) does not degrade when subjected to electron bombardment. A cross-linking enhancer (a polyfunctional vinyl or allyl compound) may be incorporated in the mixture to reduce the amount of irradiation necessary.

When heating the mixture to bring it to a formable state, it is important to heat it to a temperature above that necessary to melt the polycaprolactone (above 60° C.), but not to a temperature greater that the melting temperature of the polyethylene. If the polyethylene melts, the entire thixotropic effect is lost.

The effects of radiation cross-linking on the properties of the molten polymer of the invention are quite remarkable. This can be demonstrated on strips of the plastic, ½"×4"×1/16". These are placed in water at 70° C. until molten after which they are suspended from one end. The control sample, not irradiated, flows under its own weight until the lower end reaches the floor. At low dosages (around 5 megarads) the flow still occurs but perceptibly slower. Higher dosages are sufficient to eliminate flow. At around 15 megarads the melt is elastic. If distorted manually and then released, it returns to its original dimensions. The stiffness of the elastic melt or, more properly, its modulus of elasticity can also be varied. A highly cross-linked sample made by using high dosages distorts less at a given stress level than one made at lower radiation levels.

The radiation dosage required to effect cross-linking can be markedly reduced, if certain additives are incorporated into the poly (epsilon-caprolactone). The effective additives are chemicals containing two or more double bonds in each molecule. The presence of the trimethacrylate of trimethylolpropane at a concentration of two percent in poly (epsilon-caprolactone) reduces the dosage of irradiation required to cross-link the polymer by at least a factor of four. Other polyunsaturated molecules, such as the polyfunctional acrylates and methacrylates of polyols, neoprene and butadiene rubbers are also useful to promote the cross-linking reaction.

It is clear that inexpensive fillers can be employed along with electron irradiation or other means of cross-linking to achieve a lower cost product. It is readily apparent that, by use of cross-linking, the rheological characteristics of poly (epsilon-caprolactone) in its molten form can be modified as desired to suit the needs of the application to be considered. For general use in fabricating splints and similar structures a product with some elasticity is desired. It can be readily stretched over the member to be fitted and held in place until it becomes immobile by crystallization. If perchance, the initial fitting is not suitable, the deformed piece can be brought back to its original shape by simply replacing it in hot water. It is then ready for reuse.

In applying the cross-linked poly (epsilon-caprolactone) polyethylene mixture to the body member to be immobilized, it should be noted that excellent conformity to the shape of the body member without pressure points, etc., is readily achieved. The elasticity of the melt allows easy stretching over protuberances and close fit to adjacent areas. In general, it is easier to achieve good conformity to body members with the elastic melt than it is with any of the prior art materials used for this purpose.

Another advantage of the elasticized material is that it is less sensitive to temperature in the molten form than the prior art materials. As is well known, elastic distortion is a much lower activation energy process than viscous flow. Viscosity decreases rapidly with increasing temperature, whereas the elastic modulus decreases only moderately with increasing temperature. Hence, the temperature to which the elastic material is heated is not narrowly critical. Also, it is not necessary to achieve a uniform temperature in the melt. This allows one to use less sophisticated heating equipment. For example, it has been noted that the water in an unstirred electric frying pan tends to be hottest directly above the heating element. No adverse effect of the non-uniform temperature is noted with the cross-linked poly (epsilon-caprolactone). On the other hand, difficulties with this type of equipment are found with the prior art materials.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. An orthopedic cast, comprising a mixture of poly (epsilon-caprolactone) having a formula

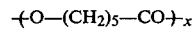

$$+O-(CH_2)_5-CO+_x$$

where x makes the weight average molecular weight greater than 5,000 with polyethylene in an amount in the range from 15% to 30%, the mixture having a softening temperature in the range from 50° C. to 100° C. with a half-time crystallization at 36° C. of between 0.5 minute and 10.0 minutes.

2. An orthopedic cast as recited in claim 1, wherein the mixture is in the form of a pre-formed cast.

3. An orthopedic cast as recited in claim 1, wherein the mixture is coated on a substrate, the substrate being a solid at the melting point of the poly (epsilon-caprolactone).

4. An orthopedic cast as recited in claim 1, wherein the substrate is a netting and the mixture is coated around each strand of the netting to form a foraminous sheet.

5. A method of forming an orthopedic cast comprising the steps of:
   (a) forming a preform sheet of a mixture of high density polyethylene with poly (epsilon-caprolactone) of weight average molecular weight greater than 5,000 having a melting point of between 50° C. and 100° C., the polyethylene being present in an amount in the range from 30% to 10% by weight,
   (b) heating the sheet to its softening point,
   (c) forming the sheet into a desired shape, and
   (d) allowing the sheet to cool below its melting point.

6. A method as recited in claim 5, wherein the sheet is heated by immersing it in water at a suitable temperature.

7. A method as recited in claim 5, wherein the sheet contains the said mixture with 2% triallyl cyanurate and a trace concentration of an anti-oxidant.

8. Method of forming an orthopedic cast, comprising the steps of:
   (a) compounding a mixture of high density polyethylene and polycaprolactone with a cross-linking enhancer and an anti-oxidant in a mixer, the polyethylene being present in an amount in the range from 10% to 30% by weight, the polyethylene and the polycaprolactone having generally similar melt indices,
   (b) forming the mixture into a preform sheet,
   (c) heating the sheet to its softening point, the temperature being maintained in the range between the melting temperature of the polycaprolactone and the melting temperature of the polyethylene to maintain a thixotropic effect,
   (d) forming the sheet into a shape, and (e) allowing the sheet to cool below its melting point.

9. Method of forming an orthopedic cast as recited in claim 8, wherein the sheet is subjected to electron radiation in the range from 0.5 to 15.0 megarads.

10. Method of forming an orthopedic cast as recited in claim 8, wherein the polyethylene is present in the amount of 25% by weight, has a melt index greater than 10, and has a density greater than 0.940 wherein the polycaprolactone is present in the amount of 73%, wherein the enhancer is triallyl cyanurate in the amount of 2% by weight, and wherein a trace amount of an anti-oxidant is present.

* * * * *